United States Patent [19]

Takamizawa

[11] Patent Number: 5,231,573
[45] Date of Patent: Jul. 27, 1993

[54] METHOD AND SYSTEM FOR ACQUIRING FLOW VELOCITIES IN ULTRASOUND DIAGNOSIS APPARATUS

[75] Inventor: Kinya Takamizawa, Utsunomiya, Japan

[73] Assignee: Kabushiki Kaisha Toshiba, Kawasaki, Japan

[21] Appl. No.: 516,909

[22] Filed: Apr. 30, 1990

[30] Foreign Application Priority Data

May 20, 1989 [JP] Japan .................................. 1-113301

[51] Int. Cl.⁵ .............................................. G06F 15/00
[52] U.S. Cl. ................................. 364/413.25; 73/602; 128/661.08; 128/660.01
[58] Field of Search ............... 364/413.25; 128/661.08, 128/661.1, 660.01, 660.07, 661.09, 662.01; 73/602

[56] References Cited

U.S. PATENT DOCUMENTS

| | | |
|---|---|---|
| 4,217,909 | 8/1980 | Papadofrangakis et al. ... 128/661.01 |
| 4,257,278 | 3/1981 | Papadofrangakis et al. .... 128/661.1 |
| 4,318,413 | 3/1982 | Iinuma et al. .................. 128/661.01 |
| 4,398,540 | 8/1983 | Takemura et al. .................. 128/660 |
| 4,641,668 | 2/1987 | Namekawa ...................... 128/661.09 |
| 4,785,402 | 11/1988 | Matsuo et al. .................. 364/413.25 |
| 4,821,574 | 4/1989 | Takamizawa ........................ 73/602 |
| 4,873,985 | 10/1989 | Nakajima ....................... 128/660.05 |
| 4,993,418 | 2/1991 | Weaver et al. ................. 128/661.08 |

*Primary Examiner*—Roy N. Envall, Jr.
*Assistant Examiner*—Laura Brutman
*Attorney, Agent, or Firm*—Finnegan, Henderson, Farabow, Garrett & Dunner

[57] ABSTRACT

In an ultrasound diagnosis apparatus, a plurality of transducers arranged in an ultrasound probe are classified into two transducer groups. By using a parallel simultaneous reception method, ultrasound beams from an observation point of an object to be examined along a transmitting direction of an ultrasound beam are received by the transducer groups. In other words, echo signals from different directions at the observation point are received. Flow velocities are respectively calculated on the basis of the echo signals received by the transducer groups, and the calculated flow velocities are added and averaged.

10 Claims, 8 Drawing Sheets

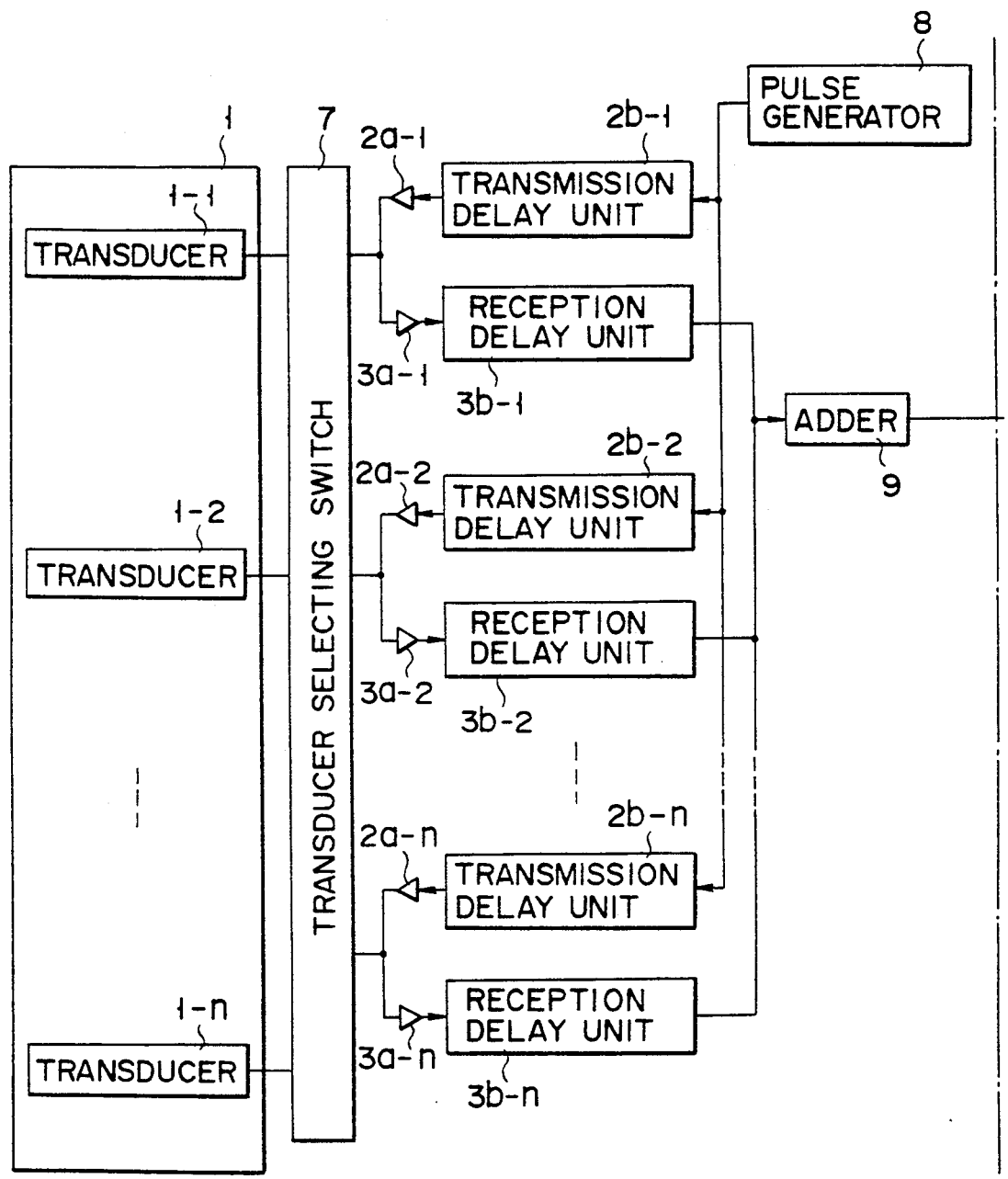
F I G. 1A

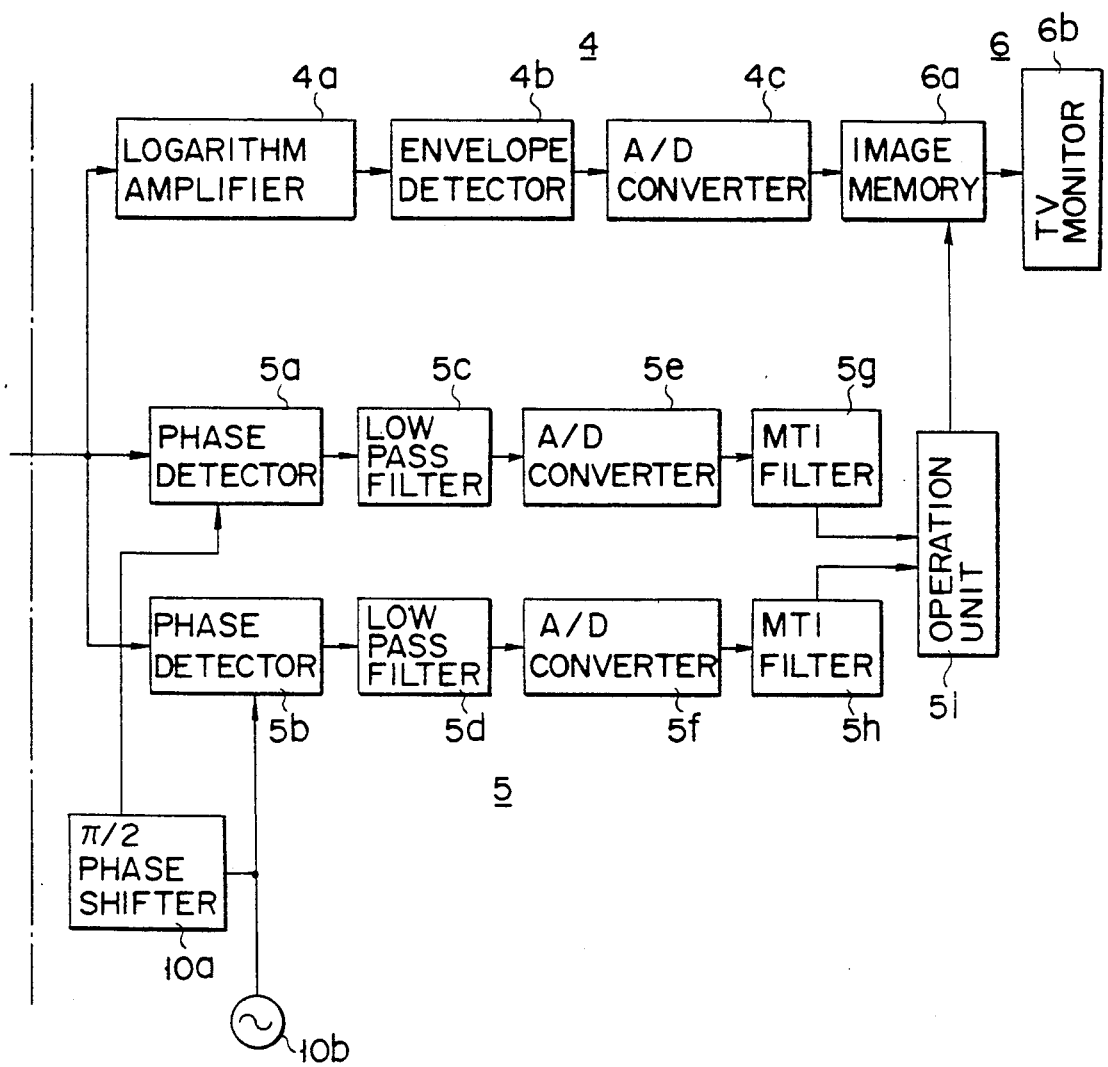
F I G. 1B

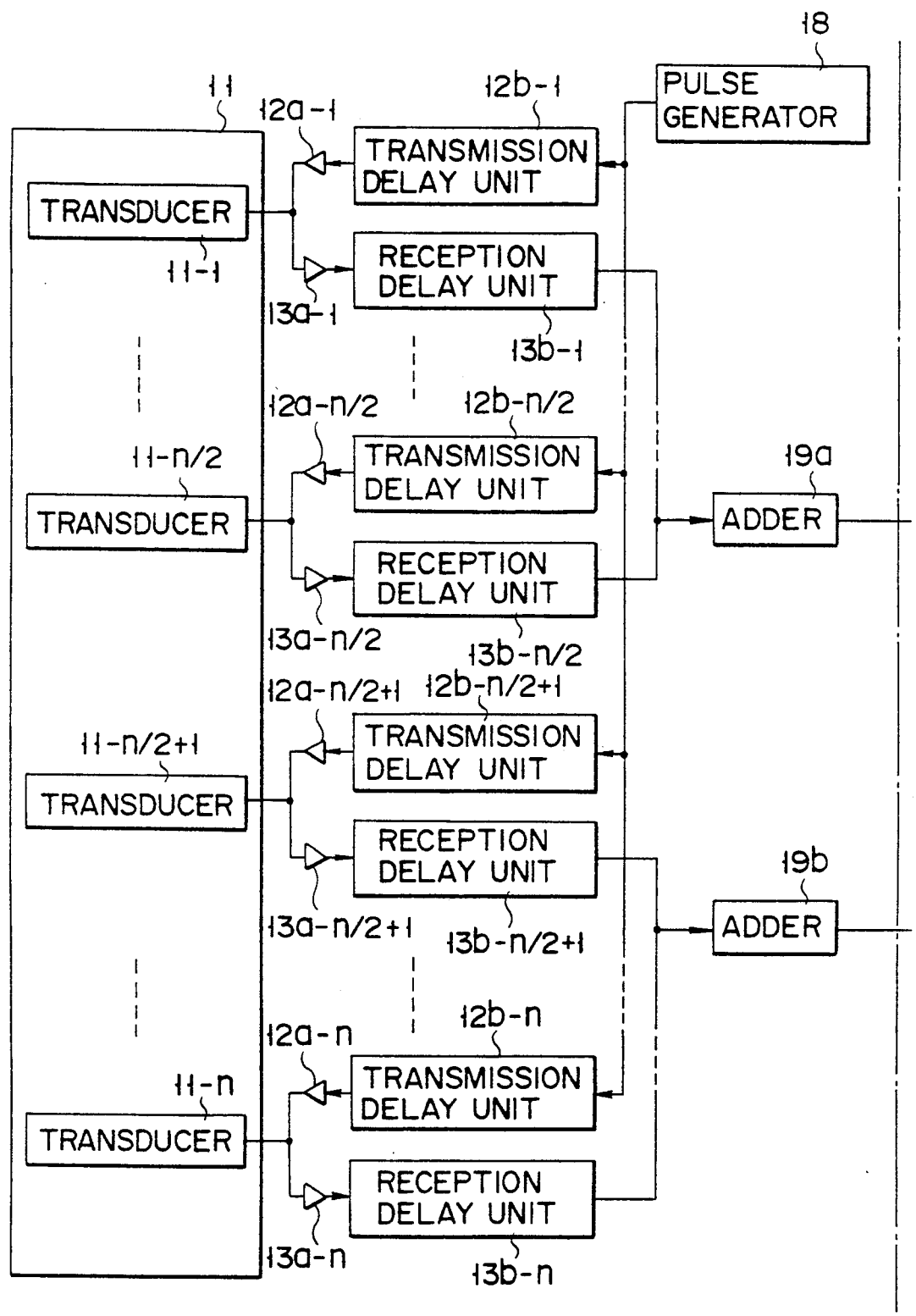
F I G. 3A

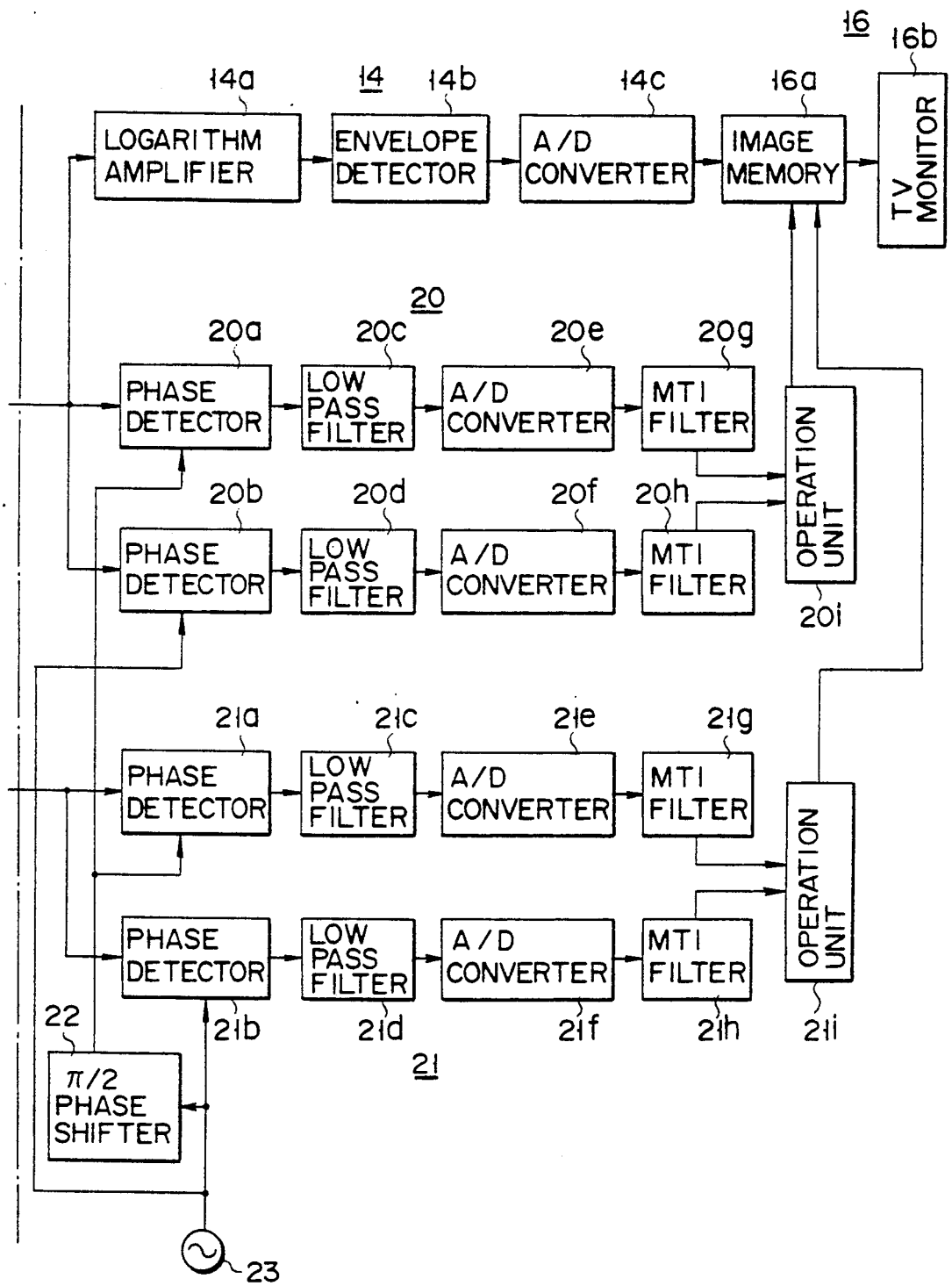
F I G. 3B

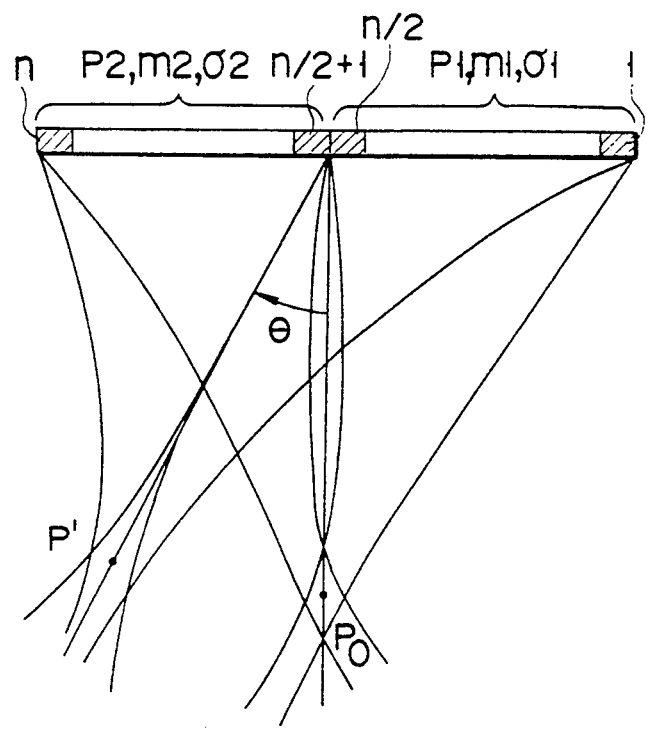
F I G. 4
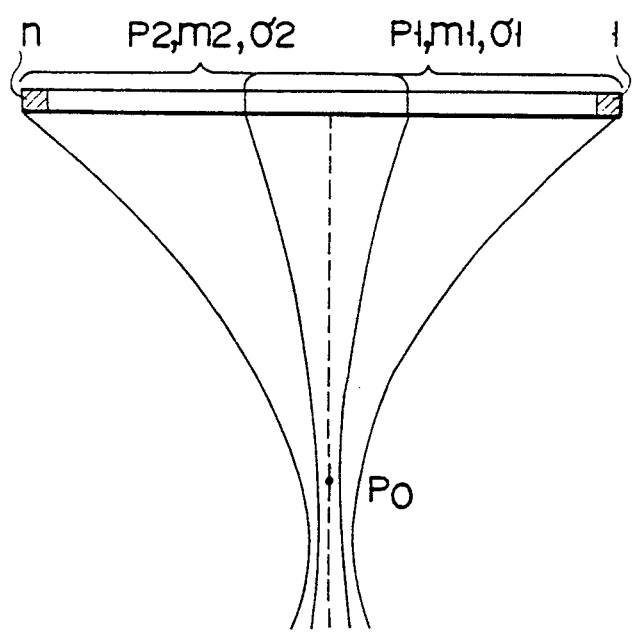
F I G. 5

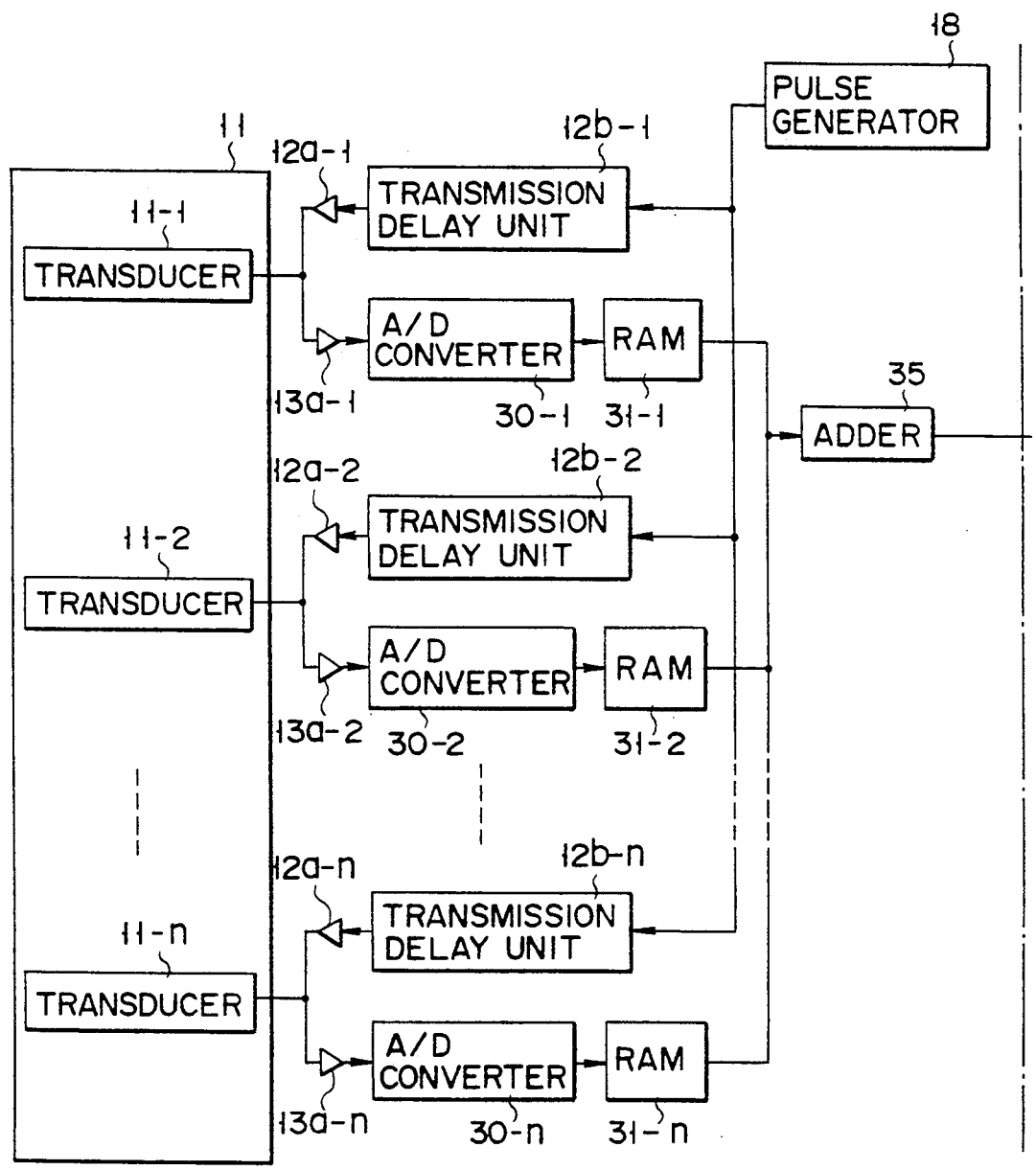
F I G. 6A

METHOD AND SYSTEM FOR ACQUIRING FLOW VELOCITIES IN ULTRASOUND DIAGNOSIS APPARATUS

BACKGROUND OF THE INVENTION

1. Field of the Invention

The present invention relates to a method and system for acquiring flow velocities in an ultrasound diagnosis apparatus.

2. Description of the Related Art

In an ultrasound diagnosis method of transmitting an ultrasound beam to a living body, and receiving waves reflected from tissues of the living body to acquire information of the living body, information associated with soft tissues can be acquired without radiation hazards caused by X-rays and without the use of a contrast medium.

An array type piezoelectric transducer is used for an ultrasound probe in a recent ultrasound diagnosis apparatus. Ultrasound beams generated by transducers of the ultrasound probe are transmitted to a living body. Since an echo signal received from the living body by the transducers is delayed by a predetermined time period, the ultrasound beams are focused on a predetermined determined position in the living body, and hence directional resolution is improved. Therefore, a high-resolution ultrasound tomographic image can be acquired.

In a linear electronic scanning type ultrasound blood flow measurement apparatus shown in FIGS. 1A and 1B, a repeating pulse signal for determining a transmission interval of the ultrasound beam is input from a pulse generator 8 to transmission delay units 2b-1 to 2b-n. In the transmission delay units 2b-1 to 2b-n, the repeating pulse signals delayed by the predetermined delay times determined on the basis of a transmitting direction and focal point of the ultrasound beams are input to pulsers 2a-1 to 2a-n for respectively generating drive pulse signals for driving transducers 1-1 to 1-n of an ultrasound probe 1. When the drive pulse signals are respectively supplied to the transducers 1-1 to 1-n by a transducer selecting switch 7, the ultrasound beams are transmitted to the living body.

On the other hand, the ultrasound beams reflected from the living body are received by the transducers 1-1 to 1-n as echo signals. The received echo signals are respectively input to preamplifiers 3a-1 to 3a-n through the transducer selecting switch 7, and are amplified to have predetermined amplitudes. In reception delay units 3b-1 to 3b-n, the echo signals are delayed by delay times substantially equal to the delay times in the transmission delay units 2b-1 to 2b-n. In an adder 9, addition of the echo signals delayed by the predetermined delay times is performed. The added echo signal is input to B- and D-mode processing units 4 and 5.

In a logarithm amplifier 4a in the B-mode processing unit 4, logarithm conversion corresponding to the amplitude of the echo signal is performed. In an envelope detector 4b, an envelope of the echo signal is detected, and is A/D-converted by an A/D (analog/digital) converter 4c. Thereafter, the converted signal is stored in an image memory 6a of a display unit 6. An ultrasound tomographic image is displayed on a TV monitor 6b.

In the D-mode processing unit 5, a reference signal having a frequency substantially equal to that of the echo signal is input from a reference signal generator 10b to a phase detector 5b. In addition, a shift signal obtained by phase-shifting the reference signal by 90° by a phase shifter 10a is input to a phase detector 5a. In the phase detectors 5a and 5b, the phase of the echo signal output from the adder 9 is detected on the basis of the shift and reference signals. The echo signals having phases different from each other by 90° are input to MTI (moving target indicator) filters 5g and 5h through low pass filters 5c and 5d, and A/D converters 5e and 5f, respectively.

When a Doppler signal is acquired, a phase shift amount (Doppler shift amount) within a unit time period of the echo signal is acquired by scanning the same portion at a predetermined interval. For example, a predetermined number of scanning operations are performed with respect to the same portion, and further a blood flow velocity at a predetermined depth is calculated on the basis of the echo signals obtained by performing a predetermined number of scanning operations with respect to the same portions. Note that each echo signal includes not only echo signals (Doppler signals) reflected from a moving object such as blood corpuscles, but also echo signals from a fixed reflector.

In order to eliminate the echo signals (clutter signals) from the fixed reflector, a predetermined number of echo signals at a predetermined depth are input to the MTI filters 5g and 5h. Note that the MTI technique is generally known in the field of radars. The clutter signals are eliminated by the MTI filters 5g and 5h, and the echo signals (Doppler signals) from only the blood corpuscles are input to an operation unit 5i. In the operation unit 5i, a frequency analysis is performed on the basis of the echo signals from which the clutter signals are eliminated, and the center or dispersion of the spectrum is calculated. The calculated value is stored in the image memory 6a. A tomographic image and a blood flow image (Doppler image) are displayed on the TV monitor 6b.

When a blood flow velocity of a predetermined portion is observed, it is generally known that the larger the number of echo signals reflected from the same portion is, the higher the precision of measurement. In particular, when a clutter signal must be sufficiently eliminated (e.g., when the clutter signal is extremely large or the frequency of the Doppler signal is close to the frequency of the clutter signal), a large number of echo signals must be acquired. The acquisition time period of the Doppler image is, therefore, longer than that of the B-mode image. For this reason, in a sector scanning operation, a parallel simultaneous reception method is used as a method of executing real time processing.

In the parallel simultaneous reception method in the sector scanning operation, as shown in FIG. 2, two receiving directions b1 and b2 are set with respect to a transmitting direction a of the ultrasound beam from the ultrasound probe 1. Note that two reception circuits having a reception directivity with respect to the receiving directions b1 and b2 are used. For example, an ultrasound beam having a relatively large beam width is transmitted along the transmitting direction a and the echo signals are simultaneously received along the receiving directions b1 and b2 shifted from the transmitting direction a by $\pm\Delta\theta$. By this method, scanning operations in the two directions adjacent to each other by $\Delta\theta$ are simultaneously performed. Therefore, an image acquisition time period can be half that in the conventional method.

For example, however, in color display of a blood flow image, color processing is not performed for a signal having no predetermined amplitude such as a noise signal. On the other hand, if a normal echo signal does not have a predetermined amplitude due to an influence of a speckle, color processing associated with the echo signal is not performed, and hence an image quality is undesirably degraded.

Thus, a demand has arisen for developing an ultrasound diagnosis apparatus which can display a blood flow image in real time without degradation of an image quality due to a speckle.

SUMMARY OF THE INVENTION

It is an object of the present invention to provide a method and system for acquiring flow velocities in an ultrasound diagnosis apparatus.

According to one aspect of the present invention, there is provided a method for acquiring flow velocities in an ultrasound diagnosis apparatus, the method comprising the steps of:

transmitting ultrasound beams to a view point of a subject;

receiving echo signals from the view point at the same time, the echo signals being received from a plurality of receiving directions;

adding the received echo signals for each of the receiving directions;

acquiring the flow velocities for each of the added echo signals; and averaging the acquired flow velocities.

According to another aspect of the invention, there is provided a system for acquiring flow velocities in an ultrasound diagnosis apparatus, the system comprising:

an ultrasound probe having a plurality of transducers, the transducers being divided into a plurality of transducer groups, one of the transducer groups being driven to transmit the ultrasound beams to a view point of the subject, and each of the transducer groups being driven to receive echo signals from the view point at the same time;

adding means for adding the echo signals for each of the transducer groups;

acquiring means for acquiring the flow velocities for each of the transducer groups in accordance with the added echo signals; and averaging means for averaging the flow velocities.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 1A and 1B are block diagrams showing an arrangement of an ultrasound blood flow measurement apparatus;

FIGS. 3A and 3B are block diagrams showing an arrangement of a system according to the first embodiment of the present invention;

FIGS. 4 and 5 are views for explaining a scanning operation in the present invention; and FIGS. 6A and 6B are block diagrams showing an arrangement of a system according to the second embodiment.

DETAILED DESCRIPTION OF THE PREFERRED EMBODIMENTS

Figure 2:
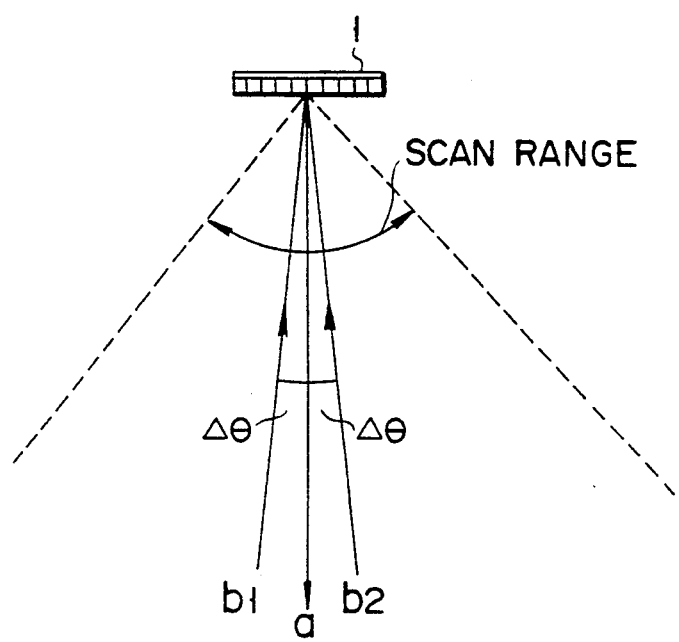
FIG. 2 is a view for explaining a parallel simultaneous reception method in a sector scan.

Referring to FIGS. 3A and 3B, a system according to the first embodiment includes an ultrasound probe 11 having transducers 11-$l$ to 11-$n$, pulsers 12$a$-$l$ to 12$a$-$n$, transmission delay units 12$b$-$l$ to 12$b$-$n$, preamplifiers 13$a$-$l$ to 13$a$-$n$, reception delay units 13$b$-$l$ to 13$b$-$n$, a pulse generator 18, adders 19$a$ and 19$b$, a B-mode (tomographic image display mode) processing unit 14, D-mode (Doppler image display mode) units 20 and 21, a display unit 16, a $\pi/2$ phase shifter 22, and an oscillator 23.

The pulse generator 18 generates a repeating pulse signal for determining a transmission interval of ultrasound beams.

The transmission delay units 12$b$-$l$ to 12$b$-$n$ delay the generated repeating pulse signal by predetermined delay times determined on the basis of a transmitting direction and focal point of the ultrasound beams.

The pulsers 12$a$-$l$ to 12$a$-$n$ generate drive pulse signals for driving the transducers 11-$l$ to 11-$n$, respectively.

The transducers 11-$l$ to 11-$n$ are classified into two transducer groups 11-$l$ to 11-$n/2$ and 11-$n/2+1$ to 11-$n$, and transmit/receive ultrasound beams. The ultrasound beams reflected from a predetermined observation point in correspondence with the transmitted ultrasound beams are simultaneously received from different directions by the transducer groups 11-$l$ to 11-$n/2$ and 11-$n/2+1$ to 11-$n$ as echo signals.

The reception delay units 13$b$-$l$ to 13$b$-$n$ delay the echo signals from the preamplifiers 13$a$-$l$ to 13$a$-$n$ by delay times substantially equal to the delay times in the transmission delay units 12$b$-$l$ to 12$b$-$n$.

The adders 19$a$ and 19$b$ add signals output from reception delay unit groups 13$b$-$l$ to 13$b$-$n/2$ and 13$b$-$n/2+1$ to 13$b$-$n$.

The B-mode processing unit 14 includes a logarithm amplifier 14$a$, an envelope detector 14$b$, and an A/D (analog/digital) converter 14$c$.

The D-mode processing unit 20 includes phase detectors 20$a$ and 20$b$, low pass filters 20$c$ and 20$d$, A/D converters 20$e$ and 20$f$, MTI filters 20$g$ and 20$h$, and an operation unit 20$i$. In addition, the D-mode processing unit 21 includes phase detectors 21$a$ and 21$b$, low pass filters 21$c$ and 21$d$, A/D converters 21$e$ and 21$f$, MTI filters 21$g$ and 21$h$, and an operation unit 21$i$.

The display unit 16 is constituted by an image memory 16$a$ and a TV monitor 16$b$, and displays tomographic and Doppler images.

An operation of this system will be described hereinafter.

When the ultrasound probe 11 having the transducers 11-$l$ to 11-$n$ is driven, an ultrasound beam is transmitted to an object to be examined along a predetermined direction. The ultrasound beams reflected from the object are received by the two transducer groups 11-$l$ to 11-$n/2$ and 11-$n/2+1$ to 11-$n$ from different directions as echo signals. The received echo signals are delayed by the two reception delay unit groups 13$b$-$l$ to 13$b$-$n/2$ and 13b-n/2+1 to 13b-n by predetermined delay times, and are added by the adders 19a and 19b. Thereafter, the added signals are input to the D-mode processing units 20 and 21, respectively.

In the D-mode processing units 20 and 21, the added signals output from the adders 19a and 19b are input to the operation units 20i and 21i through the phase detectors 20a and 20b, and 21a and 21b, the low pass filters 20c and 20d, and 21c and 21d, the A/D converters 20e and 20f, and 21e and 21f, and the MTI filters 20g and 20h, and 21g and 21h, respectively.

In the operation units 20i and 21i, blood flow velocities are calculated on the basis of the plurality of echo signals received from the same portion. As shown in FIG. 4, a power value P, a mean value m, and a standard deviation $\sigma$ are calculated as follows:

$$m = (m1 + m2)/2 \quad (1)$$

$$\sigma = (\sigma1^2 + \sigma2^2)/2 \quad (2)$$

$$P = (P1 + P2)/2 \quad (3)$$

where P1, m1, and $\sigma$1 are respectively the power value, the mean value, and the standard deviation of a blood flow velocity at a predetermined portion (to be referred to as an observation point P0) of an object on the basis of the echo signals received by the transducers 11-l to 11-n/2, and P2, m2, and $\sigma$2 are respectively the power value, the mean value, and the standard deviation of a blood flow velocity at the same observation point P0 on the basis of the echo signals received by the transducers 11-n/2+1 to 11-n.

Note that when the calculated power value of the blood flow velocity is small, an S/N ratio has been conventionally improved by blanking a blood flow image. According to this embodiment, however, when blanking is performed for the power value P using equation (3), an influence of a speckle can be decreased.

In addition, in the operation units 20i and 21i, color processing is performed on the basis of the comparison result of the obtained power value P and the predetermined value. More specifically, when the power value P is larger than the predetermined value, color processing is performed for the echo signal corresponding to the power value P.

Note that when, e.g., a blood flow velocity is continuously measured along the direction of depth, i.e., a transmitting direction of the ultrasound beam, a dynamic focus method is used. According to this method, even if the depths of the observation points are different from each other, the echo signals from the depths of the observation points are respectively received by the transducer groups 11-l to 11-n/2 and 11-n/2+1 to 11-n. In particular, by using the digital reception delay units, a high-precision dynamic focusing can be realized.

On the other hand, in order to display a two-dimensional image of a blood flow distribution, an echo signal along direction perpendicular to the transmitting direction of an ultrasound beam must be acquired. For example, when reception delay times are controlled by the reception delay units 13b-l to 13b-n in a sector scan, the echo signals respectively received by the transducer groups 11-l to 11-n/2 and 11-n/2+1 to 11-n are reflected from an observation point P' on the central axis of the transmitted ultrasound beam deflected by $\theta$, as shown in FIG. 4.

Thus, when a blood flow velocity at the predetermined observation point of the object is acquired, a power value, a mean value, and a standard deviation can be obtained in the echo signals from different directions. The number of echo signals which can be obtained within a unit time period is, therefore, twice that of the conventional apparatus.

More specifically, in measurement of a blood flow velocity at the observation point, a scanning operation is conventionally performed, e.g., ten times to acquire a blood flow velocity. According to the present invention, a precision substantially the same as that in the conventional apparatus can be obtained by performing the scanning operation five times in accordance with a parallel simultaneous reception method. In addition, an influence of a speckle which causes degradation of an image quality can be decreased.

As shown in FIG. 4, when the transducers are classified into the two transducer groups 11-l to 11-n/2 and 11-n, an S/N ratio is reduced due to degradation of a reception sensitivity. As shown in FIG. 5, therefore, the transducer groups 11-l to 11-n/2 and 11-n/2+1 to 11-n can be partially used in common.

A system according to the second embodiment will be described hereinafter.

Figure 6B:
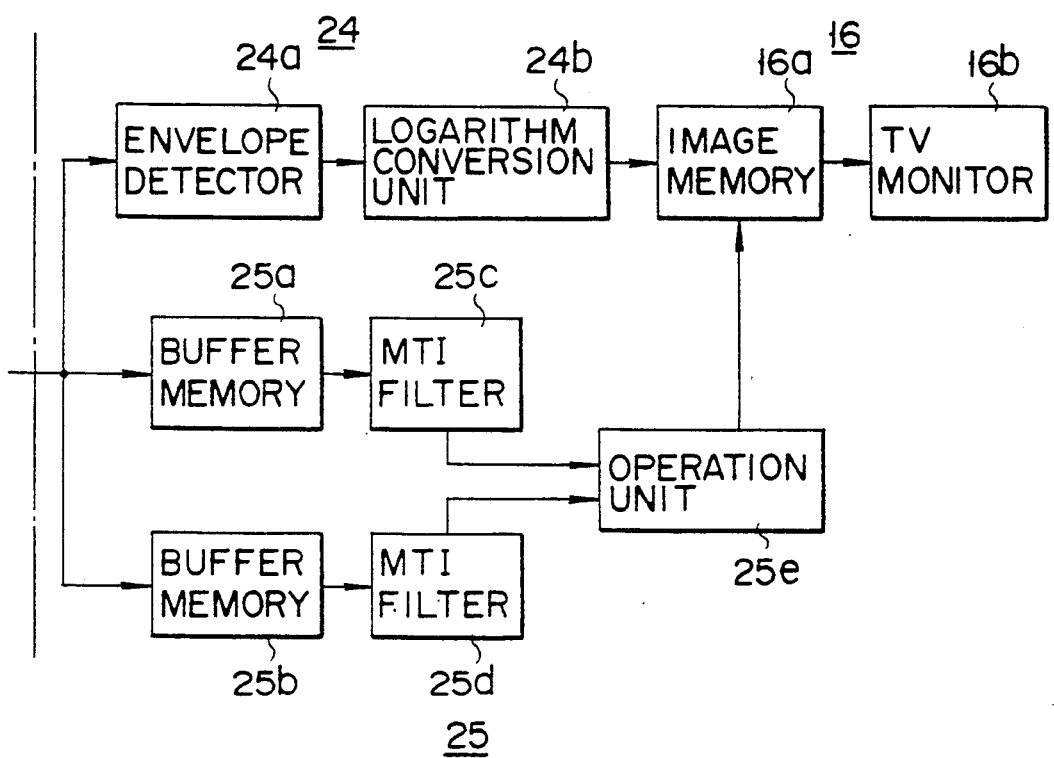

As shown in FIGS. 6A and 6B, the system of the second embodiment obtained by digitizing a reception section includes an ultrasound probe 11 having transducers 11-l to 11-n, pulsers 12a-l to 12a-n, transmission delay units 12b-l to 12b-n, preamplifiers 13a-l to 13a-n, A/D converters 30-l to 30-n, RAMs (or shift registers) 31-l to 31-n, a pulse generator 18, an adder 35, a B-mode processing unit 24, a D-mode processing unit 25, and a display unit 16.

Echo signals received by the transducers 11-l to 11-n of the ultrasound probe 1 are amplified to have predetermined amplitudes by the preamplifiers 13a-l to 13a-n, respectively. Thereafter, the obtained signals are converted into digital signals by the A/D converters 30-l to 30-n, respectively. Signals output from the A/D converters 30-l to 30-n are temporarily stored in the RAMs (random access memories) 31-l to 31-n. After a predetermined time period has elapsed, the signals are input to the adder 35. The signals input to the adder 35 are digitally added to each other.

The B-mode processing unit 24 includes an envelope detector 24a having an absolute value circuit and a low pass filter, not shown, and a logarithm conversion unit 24b having, e.g, a ROM (read only memory). In the envelope detector 24a, an envelope of a signal output from the adder 35 is detected. In the logarithm conversion unit 24b, the amplitude of an output signal from the envelope detector 24a is logarithmically converted. The signal processed by the B-mode processing unit 24 is displayed on a TV monitor 16b through an image memory 16a as a B-mode image.

On the other hand the signal output from the adder 35 is stored in buffer memories 25a and 25b. The signals are input to an operation unit 25e through MTI filters 25c and 25d. In the operation unit 25e, a blood flow velocity is calculated. The signal processed by the D-mode processing unit 25 is displayed on the TV monitor 16b through the image memory 16a as a Doppler image.

In general, when an opening of the probe corresponding to the number of transducers used in a reception of the echo signal is small, an ultrasound beam width is increased, and hence a directional resolution is degraded. A B-mode image is obtained by driving n transducers, blood flow information is obtained by driving transducers classified into a plurality of groups, thereby effectively performing an ultrasound scanning operation, as in this embodiment.

Note that although a case wherein signals are simultaneously received from two directions has been described in the above embodiment, signals can be simultaneously received from, e.g., three or more directions to perform the operation.

According to the present invention, echo signals from a predetermined observation point are simultaneously received from m different directions by a plurality of transducer groups, and blood flow velocities are calculated on the basis of the Doppler frequencies of the echo signals received from the respective directions. In addition, when calculation results are added and averaged, a blood flow velocity can be measured at a precision which is substantially the same as in the conventional method, within a time period 1/m that in the conventional method. Therefore, a blood flow image can be obtained within a time period shorter than that in the conventional method. In addition, when an image reconstruction time period is substantially equal to that in the conventional method, measurement precision can be greatly improved by the present invention. Furthermore, when blood flow velocities respectively calculated on the basis of echo signals received from different directions are added and averaged, speckle can be prevented, thus improving image quality.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method for acquiring flow velocities in an ultrasound diagnosis apparatus having a probe, the method comprising the steps of:
    transmitting ultrasound beams to a view point of a subject;
    determining a plurality of ultrasound reception sections in the probe;
    receiving echo signals from the view point by the plurality of ultrasound reception sections at the same time, the echo signals being received from a plurality of receiving directions, each of the echo signals being received from each of the receiving directions by each of the ultrasound reception sections;
    adding the received echo signals in units of each of the receiving directions;
    acquiring the flow velocities in units of the added echo signals for each of the receiving directions; and
    averaging the acquired flow velocities.

2. The method according to claim 1, wherein the averaging step includes the step of reconstructing a flow velocity distribution image from the averaged flow velocities.

3. The method according to claim 2, further comprising the step of displaying the flow velocity distribution image.

4. A system for acquiring flow velocities in an ultrasound diagnosis apparatus, the system comprising:
    an ultrasound probe having a plurality of transducers, the transducers being divided into a plurality of transducer groups, the transducer groups being driven to transmit ultrasound beams to a view point of a subject, and each of the transducer groups being driven to receive echo signals from the view point at the same time;
    adding means for adding the received echo signals in units of each of the transducer groups;
    acquiring means for acquiring the flow velocities in units of the transducer groups in accordance with the added echo signals; and
    averaging means for averaging the acquired flow velocities.

5. The system according to claim 4, wherein the averaging means includes means for reconstructing a flow velocity distribution image from the averaged flow velocities.

6. The system according to claim 5, further comprising means for displaying the flow velocity distribution image.

7. The method according to claim 1, further comprising the step of determining at least one ultrasound reception section in the probe to acquire a B-mode image;
    transmitting the ultrasound beams to the view point; and
    receiving the echo signals from the view point by the determined ultrasound reception section.

8. The method according to claim 1, wherein a part of one ultrasound reception section is used as a part of another ultrasound reception section.

9. The system according to claim 4, wherein all the transducers are used as one transducer group to transmit the ultrasound beams and receive the echo signals from the view point in order to acquire a B-mode image.

10. The system according to claim 4, wherein at least one transducer in one transducer group is used as at least one transducer in another transducer group.

* * * * *

UNITED STATES PATENT AND TRADEMARK OFFICE
CERTIFICATE OF CORRECTION

PATENT NO. : 5,231,573
DATED : July 27, 1993
INVENTOR(S) : KINYA TAKAMIZAWA

It is certified that error appears in the above-indentified patent and that said Letters Patent is hereby corrected as shown below:

On the title page:

Foreign Application Priority Data, Front Page change
"May 20" to --May 2--.

Signed and Sealed this

Tenth Day of May, 1994

Attest:

BRUCE LEHMAN

*Attesting Officer*    Commissioner of Patents and Trademarks